(12) United States Patent
Schilling

(10) Patent No.: US 8,874,237 B2
(45) Date of Patent: Oct. 28, 2014

(54) DELIVERY CATHETER INCLUDING SIDE PORT AND ELECTRODES

(75) Inventor: Richard John Schilling, London (GB)

(73) Assignee: Medtronic, Inc., Minneapolis, MN (US)

( * ) Notice: Subject to any disclaimer, the term of this patent is extended or adjusted under 35 U.S.C. 154(b) by 1234 days.

(21) Appl. No.: 12/103,840

(22) Filed: Apr. 16, 2008

(65) Prior Publication Data

US 2009/0264780 A1    Oct. 22, 2009

(51) Int. Cl.
| | |
|---|---|
| *A61B 5/0402* | (2006.01) |
| *A61N 1/00* | (2006.01) |
| *A61N 1/05* | (2006.01) |
| *A61M 25/01* | (2006.01) |

(52) U.S. Cl.
CPC ........ *A61N 1/0587* (2013.01); *A61M 2025/018* (2013.01); *A61N 1/057* (2013.01); *A61N 1/0573* (2013.01); *A61N 2001/0585* (2013.01)
USPC ............ 607/122; 600/509; 600/521; 604/508

(58) Field of Classification Search
USPC .................................... 607/122–129; 606/41
See application file for complete search history.

(56) References Cited

U.S. PATENT DOCUMENTS

| | | | | |
|---|---|---|---|---|
| 4,732,158 | A | * | 3/1988 | Sadeh ........................... 600/515 |
| 5,364,376 | A | * | 11/1994 | Horzewski et al. ............ 604/528 |
| 5,462,544 | A | * | 10/1995 | Saksena et al. ................. 606/15 |
| 6,223,087 | B1 | | 4/2001 | Williams |
| 6,609,027 | B2 | | 8/2003 | Kroll et al. |
| 6,718,206 | B2 | | 4/2004 | Casavant |
| 6,937,897 | B2 | | 8/2005 | Min et al. |
| 7,027,876 | B2 | | 4/2006 | Casavant et al. |
| 7,245,973 | B2 | | 7/2007 | Liu et al. |
| 2002/0103459 | A1 | | 8/2002 | Sparks et al. |
| 2003/0032936 | A1 | | 2/2003 | Lederman |
| 2003/0212446 | A1 | | 11/2003 | Kaplan et al. |
| 2004/0054380 | A1 | | 3/2004 | Craig et al. |
| 2004/0054388 | A1 | | 3/2004 | Osypka |
| 2004/0064176 | A1 | | 4/2004 | Min et al. |

(Continued)

FOREIGN PATENT DOCUMENTS

| | | |
|---|---|---|
| WO | WO 87/04081 | 7/1987 |
| WO | 97/44083 | 11/1997 |
| WO | WO 2004/028622 A1 | 4/2004 |

OTHER PUBLICATIONS

Scherlag, Benjamin J., et al. "Catheter Technique for Recording His Bundle Activity in Man", Circulation. 1969;39: 13-18.*

(Continued)

*Primary Examiner* — Kennedy Schaetzle
*Assistant Examiner* — Erica Lee
(74) *Attorney, Agent, or Firm* — Shumaker & Sieffert, P.A.

(57) ABSTRACT

A delivery catheter, including a catheter body, a side port, a first electrode, and a second electrode, is described. The catheter body may comprise a proximal end, a distal end, and a perimeter surface. The catheter body defines a delivery lumen extending longitudinally within the catheter body. The side port is defined in the perimeter surface of the catheter body proximate the distal end and in communication with the delivery lumen. The electrodes may be adjacent to and spaced from the side port. Techniques for using the delivery catheter to identify a desired lead implantation location, e.g., via the electrodes, and implant a medical lead or other implantable element at the desired location through the delivery lumen and side port are also described.

31 Claims, 7 Drawing Sheets

(56) References Cited

U.S. PATENT DOCUMENTS

| | | | |
|---|---|---|---|
| 2004/0116878 A1* | 6/2004 | Byrd et al. | 604/263 |
| 2004/0122496 A1 | 6/2004 | Zhang et al. | |
| 2004/0215265 A1* | 10/2004 | Keizer | 607/17 |
| 2005/0267458 A1* | 12/2005 | Paul et al. | 606/41 |
| 2006/0064027 A1 | 3/2006 | Borowitz et al. | |
| 2006/0142814 A1 | 6/2006 | Laske et al. | |
| 2007/0073370 A1 | 3/2007 | Zielinski et al. | |
| 2007/0112405 A1 | 5/2007 | Williams et al. | |
| 2007/0203555 A1 | 8/2007 | Williaims | |
| 2007/0233216 A1 | 10/2007 | Liu et al. | |
| 2007/0239134 A1* | 10/2007 | Lesh et al. | 604/506 |
| 2008/0008688 A1* | 1/2008 | Stokes et al. | 424/93.21 |

OTHER PUBLICATIONS

Reply to Written Opinion from corresponding PCT Application Serial No. PCT/US2008/009026 filed Feb. 16, 2010 (11 pages).

International Search Report and Written Opinion from corresponding PCT Application Serial No. PCT/US2008/009026, mailed Feb. 3, 2009 (11 pgs.).

Daniel C. Sigg, MD, PhD et al., "Focal Pharmacological Modulation of Atrioventricular Nodal Conduction via Implantable Catheter a Novel Therapy for Atrial Fibrillation?" *Circulation, Journal of the American Heart Association*, 2006; 113; 2383-2390.

International Preliminary Report on Patentability for PCT/US2008/009026, dated Aug. 4, 2010 (10 pp.).

* cited by examiner

DELIVERY CATHETER INCLUDING SIDE PORT AND ELECTRODES

TECHNICAL FIELD

The disclosure generally relates to a delivery catheter for delivering an implantable medical lead or other implantable element to an electrical stimulation site.

BACKGROUND

Specialized groups of cardiac cells that form the cardiac conduction system control the frequency, pathway of conduction, and rate of propagation of action potentials through the heart, which cause the heart to beat in an efficient manner. This special conduction system includes the sinoatrial node (SA node), the atrial internodal tracts, the atrioventricular node (AV node), the His bundle, and the right and left bundle branches.

The SA node, located at the junction of the superior vena cava and right atrium, normally acts as the natural pacemaker, generating action potentials, which are conducted through the rest of the heart. When normal conduction pathways are intact, an action potential generated in the SA node is conducted through the atria and to the AV node via the atrial internodal tracts. The conduction through the AV nodal tissue takes longer than through the atrial tissue, resulting in a delay between atrial contraction and the start of ventricular contraction.

The AV node, located in the central fibrous body, conducts the action potential to the His bundle, located under the annulus of the tricuspid valve. The His bundle splits into the left and right bundle branches, which conduct the action potential to specialized fibers called "Purkinje fibers." The bundle branches rapidly conduct the action potential down the ventricular septum, where the Purkinje fibers spread the depolarization wavefront quickly to the remaining ventricular myocardium, producing a coordinated contraction of the ventricular muscle mass.

Conduction abnormalities may cause slowed or disrupted conduction anywhere along this conduction pathway. For example, the SA node may not generate action potentials at a fast enough rate resulting in too slow of heart rate, or bradycardia. AV block may prevent conduction of the action potential from the atria to the ventricles. A left and right bundle branch block, or other conduction abnormalities in the Purkinje fibers or ventricular myocardium, may cause the contraction of the right and left ventricles to be asynchronous. These and other conduction abnormalities may be treated by an external or implantable pacemaker.

Pacemakers are typically coupled to the heart via one or more implantable leads, each carrying one or more electrodes for stimulating the heart and for sensing the intrinsic electrical signals associated with a conducted action potential. Electrodes are commonly placed on the endocardial surface using a transvenous approach. For example, a right ventricular lead may be advanced into the right ventricle and placed such that an electrode is positioned at or near the right ventricular apex. Low capture thresholds and stable lead positioning have made the right ventricular apex a preferred ventricular stimulation site.

However, ventricular pacing at the location of the right ventricular apex does not mimic the normal ventricular conduction pathway. Both experimental and clinical studies have shown that septal pacing can improve various indices of cardiac function compared to apical pacing. Direct myocardial stimulation, as occurs in apical pacing, can cause remodeling of the ventricular myocardium, including myofibrilar disarray and local hypertrophy away from the electrode.

The most normal physiological approach to pacing the ventricles when normal AV nodal conduction fails may be to deliver electrical stimulation pulses directly to the His bundle. Depolarization of the His bundle tissue may be conducted normally through the ventricular conduction pathway, down the left and right bundle branches and to the remainder of the ventricular myocardium. The resulting ventricular contraction, which is more rapid and results in a narrow QRS complex and a more vigorous, normal contraction, may produce a better-coordinated ventricle contraction for achieving efficient heart pumping action.

In some cases, left ventricular (LV) pacing/sensing may be desired instead of, or in addition to right ventricular (RV) pacing/sensing. For example, RV and LV pacing may be provided in a time coordinated fashion to resynchronize the contraction of the ventricles, e.g., provide cardiac resynchronization therapy (CRT), which may be indicated for cardimyopathy or other ventricular conduction abnormalities. For LV pacing/sensing, a lead may be transvenously advanced through the right ventricle, into the coronary sinus and, in some cases, a coronary vein branching from the coronary sinus, to place electrodes near the myocardium of the left ventricle.

Leads may also be transvenously implanted in one or both atria. Furthermore, in some cases, cardiac pacing/sensing leads cannot be, or for some other reason are not implanted transvenously. In such cases, a lead may be epicardially implanted by fixing an electrode at the distal tip of the lead to the myocardium through an incision or puncture in the pericardium.

SUMMARY

In general, the disclosure is directed to a delivery catheter configured to facilitate identification of a desired location for implantation of a medical lead, and implantation of the lead at the desired location, as well as methods for using the delivery catheter to identify the desired location and implant a medical lead at the desired location. As one example, a delivery catheter may facilitate delivering a stimulation lead to a desired location proximate the His bundle for His bundle pacing. The delivery catheter may include a plurality of electrodes, a delivery lumen, and a side port. The electrodes may be electrically coupled to sensing circuitry, e.g., for sensing an electrocardiogram (ECG). The electrodes may be used to determine a desired implantation location, such as, for example, a desired stimulation location. Once the desired location is determined, a lead may be advanced through the delivery lumen and out the side port to the desired location.

In one embodiment, the disclosure is directed to a delivery catheter. The delivery catheter may include a catheter body, a side port, a first electrode, and a second electrode. The catheter body may comprise a proximal end, a distal end, and a perimeter surface. Further, the catheter body defines a delivery lumen extending longitudinally within the catheter body. The side port is defined in the perimeter surface of the catheter body proximate the distal end and in communication with the delivery lumen. Each of the first and second electrodes is adjacent to and spaced from the side port.

In another embodiment, the disclosure is directed to kit including a delivery catheter and an implantable element for at least one of therapy delivery or sensing. The delivery catheter may include a catheter body, a side port, a first electrode, and a second electrode. The catheter body may comprise a proximal end, a distal end, and a perimeter surface. Further, the catheter body defines a delivery lumen extending longitudinally within the catheter body. The side port is defined in the perimeter surface of the catheter body proximate the distal end and in communication with the delivery lumen. Each of the first and second electrodes is adjacent to and spaced from the side port.

In yet another embodiment, the disclosure is directed to a method that comprises advancing a delivery catheter toward a desired location within a patient. The delivery catheter comprises a catheter body including a proximal end, a distal end and a perimeter surface. The catheter body defines a delivery lumen extending longitudinally within the catheter body. The delivery catheter also includes a side port defined in the perimeter surface of the catheter body proximate the distal end and in communication with the delivery lumen. The delivery catheter further includes a first electrode and a second electrode. Each of the first and second electrodes is adjacent to and spaced from the side port. The method also includes identifying the desired location with the first electrode and the second electrode, advancing an implantable element for at least one of therapy delivery or sensing through the delivery lumen and out the side port to the desired location, and withdrawing the delivery catheter from patient.

DETAILED DESCRIPTION

In general, the present disclosure is directed to a delivery catheter and methods of using the delivery catheter. The delivery catheter may be used to deliver a sensing lead, stimulation lead or drug delivery catheter to a desired location within a patient. In general, the patient may be a human patient. However, in other embodiments, the patient may be a non-human patient. The desired location may generally include any site within the patient where stimulation, sensing, or drug delivery is desired. In some embodiments, the desired location includes a His bundle, a coronary vein, or tissue suitable for pacing, which is not dead, damaged, or otherwise not operating within general anatomical norms.

The delivery catheter may include features that facilitate determination of the desired location. For example, the delivery catheter may include at least two electrodes for sensing a waveform, such as an ECG. The desired location may be determined based on a characteristic of the waveform, such as the amplitude or the presence of certain waveform features.

The delivery catheter may also include features that facilitate delivery of the lead or drug delivery catheter at an angle to the longitudinal axis of the delivery catheter. For example, the delivery catheter may include a side port defined in a perimeter surface of the catheter, through which the lead or drug delivery catheter exits a lumen of the delivery catheter. In some embodiments, the delivery catheter may include a deflection member which deflects the lead or drug delivery catheter out of the side port.

In this disclosure, the delivery catheter will be primarily described with reference to delivering a stimulation lead to a location proximate a His bundle in a heart. However, it will be understood that delivery catheters of the present disclosure are not limited to delivering stimulation leads to a His bundle. For example, delivery catheters described herein may be used to deliver leads to a coronary vein, to epicardial tissue, or other locations. Additionally, delivery catheters described herein may be used to deliver leads for neurostimulation therapy (e.g., spinal cord stimulation), deep brain stimulation, stimulation of one or more muscles, muscle groups or organs, and, generally, stimulation of tissue of a patient. Further, in some embodiments the delivery catheters described herein can be used to deliver catheters for dispensing a drug or other beneficial agent from an implanted or external drug delivery device. In short, the delivery catheters described herein can find useful application in delivery of a wide variety of leads or catheters for delivery of therapy to a patient or patient sensing.

Figure 1:
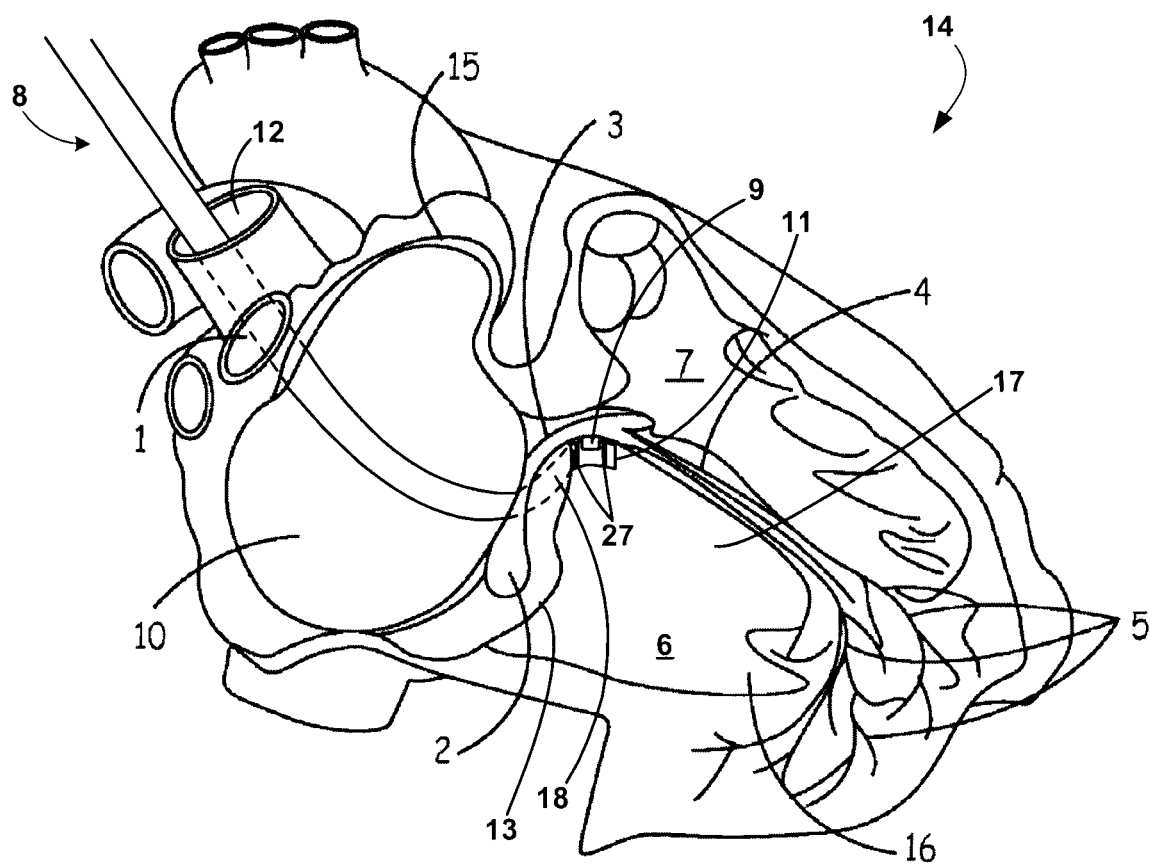
FIG. 1 is a schematic diagram illustrating a right side of a heart and includes an example delivery catheter inserted through the superior vena cava and right atrium into the right ventricle.

FIG. 1 is a schematic diagram of a right side of a heart 14 having an anterior-lateral wall peeled back to present a portion of the heart's intrinsic conduction system and chambers of a right atrium (RA) 10 and a right ventricle (RV) 6. Pertinent elements of the heart's intrinsic conduction system, illustrated in FIG. 1, include a sinoatrial (SA) node 1, an atrioventricular (AV) node 2, a His bundle 3, a right bundle branch 4, and Purkinje fibers 5. SA node 1 is shown near the superior vena cava (SVC) 12 in the RA 10. An electrical impulse starting at the SA node 1 travels rapidly through tissue of RA 10 and tissue of a left atrium (not shown) to AV node 2. At AV node 2, the impulse slows to create a delay before passing on through His bundle 3, which branches, in an interventricular septum 7, into a right bundle branch 4 and a left bundle branch (not shown) and then, near RV apex 16, into Purkinje fibers 5. Flow of the electrical impulse creates an orderly sequence of atrial and ventricular contraction and relaxation to efficiently pump blood through heart 14.

Due to disease, injury, or natural defects, the intrinsic conduction system of heart 14 may no longer operate within general anatomical norms. Consequently, a cardiac pacemaker system can be implanted into a patient such that electrodes carried by an implantable medical lead are placed in an atrial appendage 15. The electrodes stimulate RA 10 downstream of SA node 1 and the stimulating pulse travels on to AV node 2, His bundle 3, and Purkinje fibers 5 to restore physiological contraction of the heart. However, if a patient has a defective AV node 2, pacing in atrial appendage 15 will not be effective, since the pacing site is upstream of AV node 2. Such a patient may have a cardiac pacemaker system implanted such that lead electrodes are placed in an RV apex 16. RV apex 16 has been an accepted site for pacing since it is a relatively easy to engage lead electrodes at this site, and pacing from this site has been demonstrated safe and effective. Due to questions raised by recent studies looking into long-term effects of pacing from RV apex 16, as previously described, there is a great deal of interest in more physiologically correct pacing.

One site for more physiologically correct pacing is the His bundle 3. As described above, the His bundle 3 forms part of the intrinsic conduction system of heart 14, and any pacing applied from the His bundle 3 will conduct through the His bundle 3 to the Purkinje fibers 5 and throughout the right ventricle 6 and left ventricle (not shown). However, determining the location of the His bundle 3 and attaching a lead proximate to the His bundle 3 may be difficult.

For example, one preferred location from which the His bundle 3 may be paced is proximate to and under the tricuspid valve. This location may be accessed from the right ventricle, and may be difficult to reach using a distal port delivery catheter. Further, once this location is reached, it may be challenging to maintain a distal port delivery catheter in position as the lead is fixed to the His bundle 3 or tissue proximate the His bundle 3. Additionally, locating the His bundle 3 may be difficult in at least some hearts, because the His bundle 3 may not be reliably locatable in some patients using imaging techniques.

FIG. 1 illustrates a portion of an example delivery catheter 8, which includes features that may facilitate locating His bundle 3, delivering a lead to His bundle 3 or tissue adjacent His bundle 3, and fixing the lead to His bundle 3 or the adjacent tissue. For example, the delivery catheter 8 includes a side port 9 located proximate to a distal end 11 of the catheter 8 and in communication with an internal lumen 22 of delivery catheter 8 (FIG. 2B). Delivery catheter 8 also includes electrodes 27 located adjacent to and spaced from side port 9. The proximal end of delivery catheter 8 is not shown in FIG. 1.

Delivery catheter 8 may be inserted into the heart using a transvenous approach through the SVC 12 into the right atrium 10 and may be directed through the tricuspid valve 13 to RV 6. In some embodiments, delivery catheter 8 is a steerable catheter. That is, in some embodiments, the delivery catheter 8 includes features that allow it to effectively transfer force applied to a proximal end, e.g., handle, of the delivery catheter 8 into motion of a distal end of delivery catheter 8. In other embodiments, delivery catheter 8 is a guidable catheter and includes a lumen for receiving a guide wire to assist with advancing the catheter 8 into a desired position within the heart.

Delivery catheter 8 may comprise a flexible, biocompatible material such as, for example, silicone or polyurethane. In some embodiments, delivery catheter 8 may further include a radiopaque marker to facilitate fluoroscopic or other visualization of the catheter, e.g., for steering and/or orienting the catheter, as it is being delivered to the target tissue site. A length of delivery catheter 8 may vary, but may be between about 30 and 60 centimeters, with an outer diameter of less than about 10 French, or about 0.131 inches.

As illustrated in FIG. 1, a curve, multiple curves, or any other shape may be formed in a distal portion 18 of the catheter 8 proximate distal end 11 and to assist in bringing distal end 11 into contact with His bundle 3 or tissue proximate His bundle 3. In some embodiments, the curve(s) or other shape may be formed in catheter 8 through use of a guide wire (not shown) that includes the desired curve or shape, or an actuation member at a proximal end of the delivery catheter 8 that can be manipulated to induce the desired curve(s) or shape in distal portion 18. For example, in some embodiments the actuation member (not shown) may be a rotatable thumb wheel coupled to one or more pull wires attached to an off-axis attachment point near distal end 11. By actuating the rotatable thumb wheel, the pull wire(s) may be tightened, which may cause distal end 11 to deflect and induce the desired shape in distal portion 18.

In other embodiments, such as, for example, when the delivery catheter 8 is a steerable catheter, the catheter 8 may include a pre-formed curve or shape. Delivery catheter 8 may be flexible to facilitate advancement of the catheter 8 through the circulatory system (including SVC 12). Upon advancing into RA 10, catheter 8 may begin to regain its pre-formed curve or shape. The catheter 8 may then be advanced through the tricuspid valve 13 and into the right ventricle 6, where distal end 11 of catheter 8 is directed into contact with endocardial tissue proximate to His bundle 3.

Side port 9 is located on a perimeter surface 17 (FIG. 2A) of delivery catheter 8 proximate to distal end 11. In some embodiments, side port 9 may be located on a portion of the perimeter surface 17 that is inwardly oriented when the pre-formed curve of the distal portion 18 of catheter 8 is present. In other embodiments, delivery catheter 8 may be manipulated (e.g., rotated or twisted) to inwardly or outwardly orient side port 9.

Because side port 9 forms the exit through which lead 23 is advanced, in some embodiments the distal end 11 of lead may be a blind end. That is, distal end 11 may not include an orifice in communication with the internal lumen 22 of catheter 8. In other embodiments, internal lumen 22 may extend fully from proximal end of delivery catheter 8 to distal end 11 of catheter 8.

Figure 2A:
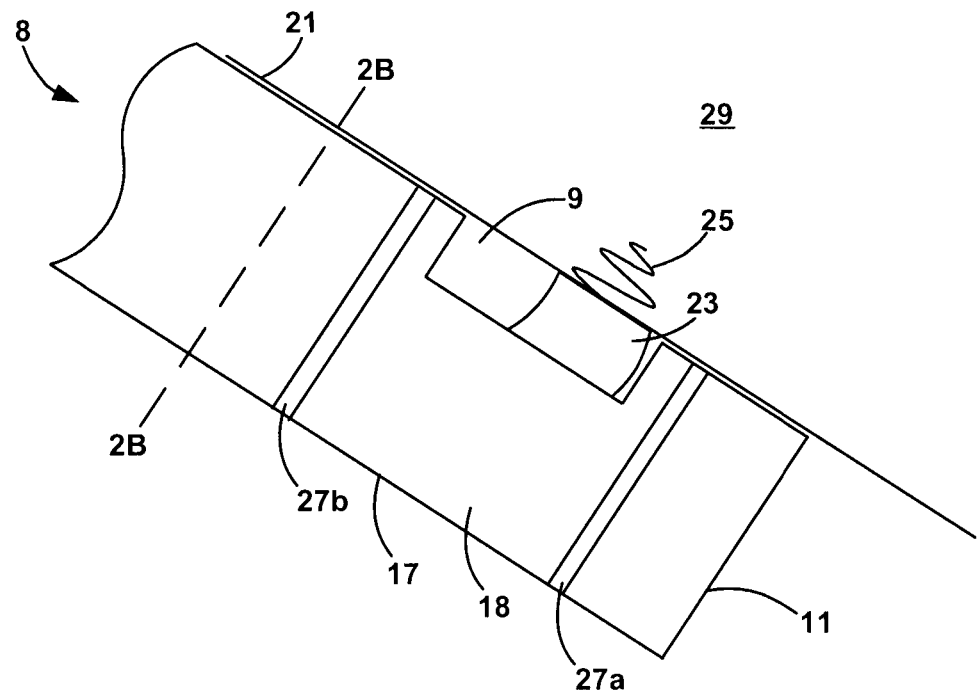
FIG. 2A is a side view illustrating the example delivery catheter of FIG. 1 and a lead exiting the catheter and attached to a surface.
Figure 2B:
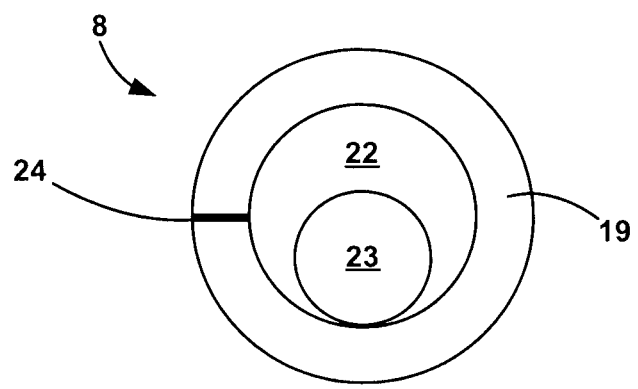
FIG. 2B is a cross-sectional view of the delivery catheter of FIG. 2A taken along line 2B.

FIG. 2A is a side view illustrating distal portion 18 of delivery catheter 8 and a lead 23 exiting the catheter and attached to a surface. FIG. 2B is a cross-sectional view of the delivery catheter 8 taken along line 2B, which is illustrated in FIG. 2A. As shown in FIG. 2A, the side port 9 may be manipulated to be proximate to surface 21 of tissue 29, which may be tissue of His bundle 3, or endocardial tissue near His bundle 3. Side port 9 provides an exit orifice through which lead 23 may exit delivery catheter 8 to be fixed to tissue 29 by fixation element 25. The side port 9 may be in communication with an internal lumen 22 (see FIG. 2B) defined within delivery catheter 8. Lead 23 may be advanced through the internal lumen 22 from a proximal end (not shown) of delivery catheter 8 to the distal end 11 of catheter 8 and exit through side port 9.

In the embodiment illustrated in FIG. 2A and FIG. 2B, the fixation element 25 is a helical fixation element, which, in some embodiments, may also function as a sensing or stimulation electrode. In other embodiments, however, another type of fixation element 25 may be used, and fixation element 25 and the electrode may be separate structures. For example, fixation element 25 may comprise a hook, a barb, an expandable fixation element, an adhesive, a tissue ingrowth element such as a mesh fiber, or a combination of more than one element. In the embodiment illustrated in FIGS. 2A and 2B, once the lead 23 exits through side port 9 and contacts surface 21, the lead body is rotated to advance the fixation element 25 through surface 21 and into the tissue 29. In other embodiments, lead 23 may be manipulated appropriately to cause fixation element 25 to attach lead 23 to tissue 29.

Delivery catheter 8 also includes a first electrode 27a and a second electrode 27b (collectively "electrodes 27"). Electrodes 27 are each located adjacent to and spaced from side port 9. In the embodiment shown in FIGS. 2A and 2B, first electrode 27a is distal from side port 9 and second electrode 27b is proximal from side port 9. In other embodiments, as described below, both electrodes 27 may be proximal or distal from side port 9. In some embodiments, each of electrodes 27 is spaced at least about 2 millimeters from an adjacent edge of side port 9.

In some embodiments, delivery catheter 8 may include conductors (not shown) that electrically couple electrodes 27 to an external device (not shown), e.g., via a connector (not shown) comprising electrical contacts on a proximal portion of catheter 8. The external device may include circuitry for receiving and conditioning physiological signals of a patient via electrodes 27. In some embodiments, the external device may include a user interface, which may comprise a display for displaying the physiological signals. In some embodiments, the external device may include circuitry, such as digital signal processor (DSP), microprocessor, application specific integrated circuit (ASIC), or other processor or processing circuitry, for processing the signal, e.g., for automatically detecting features in the signal.

In some embodiments, the physiological signal is an electrocardiogram (ECG). The external device or a user, e.g., physician, may detect the location of His bundle 3 based on the ECG waveform. For example, when the electrodes 27 are located adjacent His bundle 3, the ECG waveform may include the atrial P-wave, ventricular QRS signature, and a His spike between the P-wave and QRS signature. Thus, translating the catheter 8 along surface 21 while collecting an ECG may allow determination of a location of His bundle 3.

As an example of an embodiment in which the external device comprises a processor capable of detecting features within a physiological signal, the processor may be capable of detecting an electrical potential waveform indicative of the His bundle 3. For example, the His bundle 3 has a signature waveform with a frequency of about 200 Hz, which may be detectable by the processor.

Further, in some embodiments, the ECG may be used to differentiate between viable tissue suitable for pacing and dead (ischemic) or damaged tissue unsuitable for pacing. For example, the ECG may include a lower voltage amplitude when electrodes 27 are adjacent dead or damaged tissue compared to when electrodes 27 are adjacent viable tissue.

In some embodiments, the conductors may electrically couple the electrodes 27 to an electrical energy source, which may be part of the same external device used for signal monitoring, or a different external device. The electrical energy source may apply a voltage or current between the first electrode 27a and second electrode 27b. When electrodes 27 are in contact with surface 21 of tissue 29, the electrical energy travels through the tissue 29 and an impedance of the tissue 29 may be determined by measuring the electrical current or voltage, and calculating impedance based on the measured value and the applied voltage or current. By scanning the lead across the tissue and monitoring the impedance, the location of the His bundle 3 may be determined. Specifically, tissue comprising the His bundle 3 may exhibit a lower impedance than an impedance of adjacent endocardial tissue. In fact, an impedance of tissue of the His bundle 3 may be about 50% lower than an impedance of adjacent endocardial tissue.

In some embodiments, delivery catheter 8 also includes a feature 24 which may facilitate withdrawal of the delivery catheter 8 once lead 23 is in the desired position. For example, the feature 24 may comprise a thin silver strip which allows a physician to cut delivery catheter 8 more easily. In other embodiments, the feature 24 may comprise a thin groove or perforation that enables a physician to tear catheter, or a substantially longitudinally-oriented tear strip that a physician may use to tear catheter 8. In some embodiments, delivery catheter does not include such a feature 24.

Figure 3:
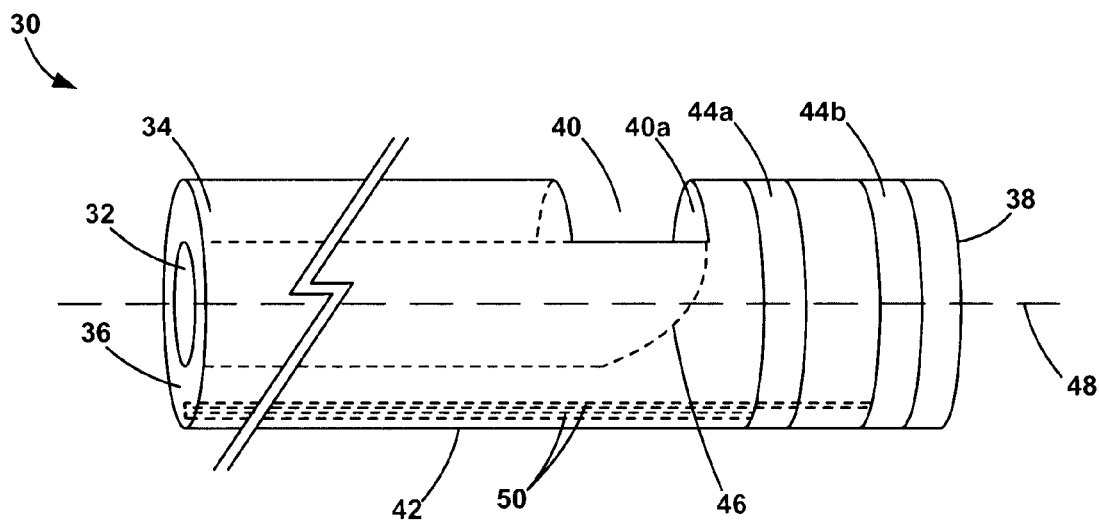
FIG. 3 is a side view illustrating another example delivery catheter.

FIG. 3 illustrates another example delivery catheter 30, which includes a single delivery lumen 32. The delivery lumen 32 is defined by the catheter body 34 and extends substantially longitudinally within catheter body 34 from catheter proximal end 36 to catheter distal end 38. The delivery catheter 30 further includes a side port 40 defined in perimeter surface 42, a first electrode 44a and a second electrode 44b (collectively "electrodes 44").

Delivery lumen 32 is in communication with side port 40. In the embodiment illustrated in FIG. 3, the delivery catheter 30 includes a deflection member 46, which is shaped to deflect a lead (e.g., lead 25) advancing substantially longitudinally through lumen 32 to extend out through side port 40. For example, the deflection member 46 may include a curved surface (FIG. 3), a sloped surface (FIG. 4), a movable flap (FIGS. 5 and 6), or the like. In some embodiments, delivery catheter 30 may not include a deflection member 46, and lumen 32 may terminate in a substantially flat wall proximate distal periphery 40a of side port 40.

In some embodiments, deflection member 46 may be shaped such that the lead exits side port 40 about orthogonal to the longitudinal axis 48 of the catheter 30. In other embodiments, deflection member 46 may be shaped such that the lead exits side port 40 at a non-orthogonal angle to longitudinal axis 48 of catheter 30.

FIG. 3 also illustrates electrodes 44 both located adjacent to and separated from side port 40. In FIG. 3, each of electrodes 44 is located distal from port 40, and is electrically coupled to a respective one of conductors 50, which extend to proximal end 36 of delivery catheter 36. While not shown in FIG. 3, conductors 50 may include, at their proximal ends, connectors for electrically connecting to an external device, such as a monitor, display, ECG machine, voltage source or waveform detector, as described above.

Figure 4:
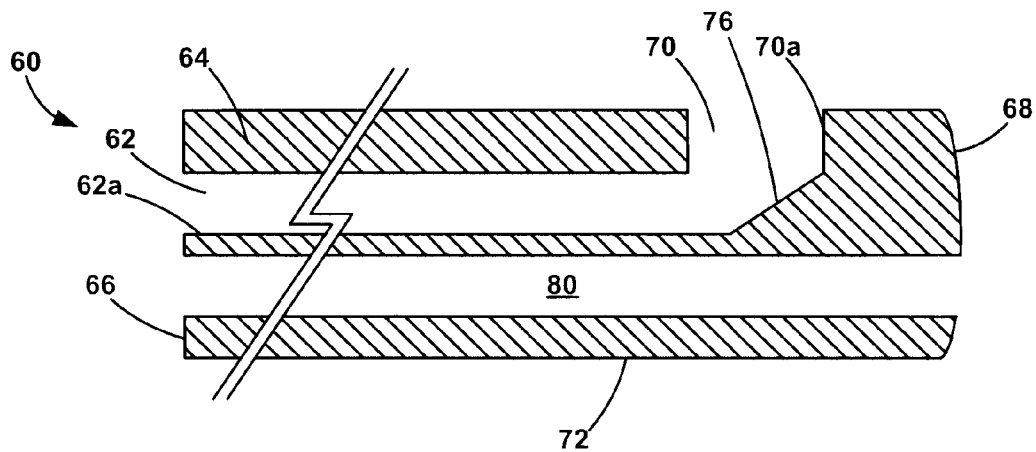
FIG. 4 is a cross-sectional side view illustrating another example delivery catheter including a guide wire lumen.

FIG. 4 illustrates a cross-sectional view of another example embodiment of a delivery catheter 60. Certain aspects of catheter 60 are similar to catheter 8 and catheter 30 of FIGS. 1, 2 and 3. For example, delivery catheter 60 includes a catheter body 64, which defines a delivery lumen 62 extending substantially longitudinally within catheter body 64 from a catheter proximal end 66 substantially to a catheter distal end 68. Delivery catheter 60 further includes a side port 70, defined in perimeter surface 72, in communication with delivery lumen 62. Catheter body 64 also includes a deflection member 76, which in the embodiment illustrated in FIG. 4, is a sloped surface connecting distal periphery 70a of side port 70 with a catheter lumen wall 62a. Deflection member 76 may deflect a lead advanced through delivery lumen 62 out through side port 70.

Delivery catheter 60 further includes a guide wire lumen 80 defined by catheter body 64 and extending substantially longitudinally from catheter proximal end 66 to catheter distal end 68. Guide wire lumen 80 may receive a guide wire for guiding the delivery catheter 60 into a desired position, such as into a desired position in a right ventricle of a heart.

Figure 5:
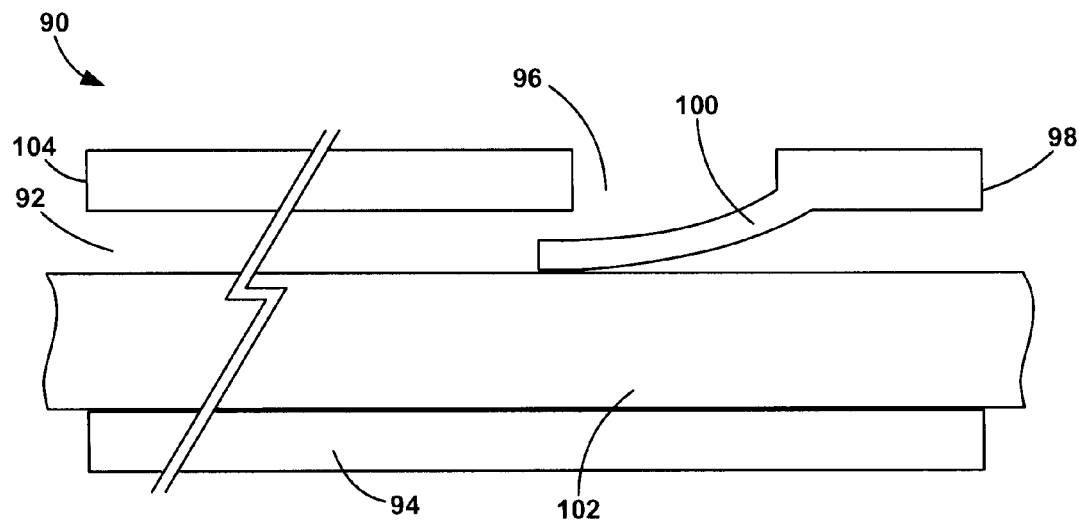
FIG. 5 is a cross-sectional side view illustrating another example delivery catheter including a movable deflection member and a guide wire disposed in the catheter.
Figure 6:
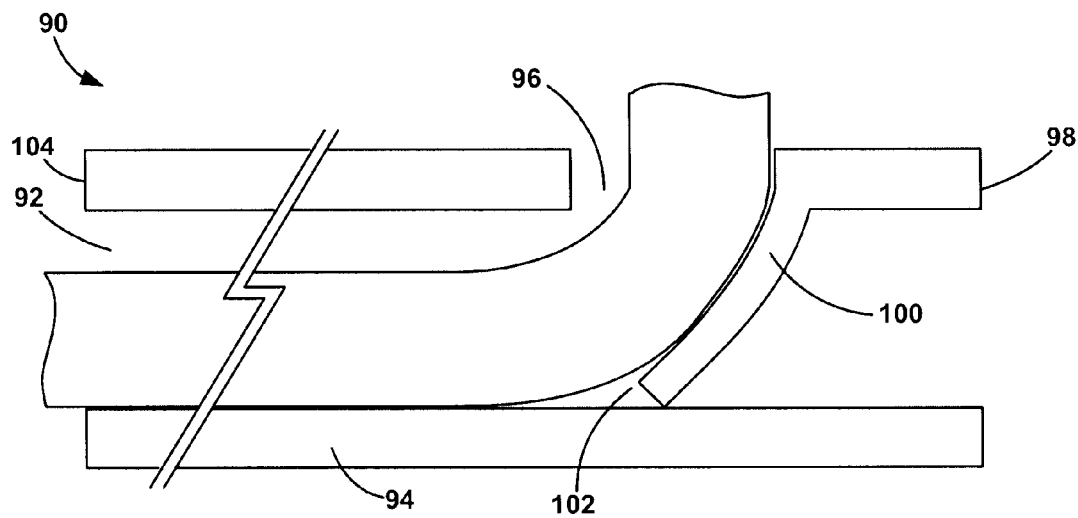
FIG. 6 is a cross-sectional side view illustrating the delivery catheter including the movable deflection member of FIG. 5 and a lead advanced through the catheter.

FIGS. 5 and 6 illustrate an example delivery catheter 90 including a single delivery lumen 92 defined in catheter body 94. Delivery lumen 92 extends fully from catheter proximal end 104 to catheter distal end 98. The delivery catheter 90 further includes a deflection member comprising a movable flap 100. Movable flap 100 may be used to provide a single lumen delivery catheter 90 that is capable of receiving a guide wire 102.

In the embodiment illustrated in FIGS. 5 and 6, the guide wire 102 may first be advanced to proximate the desired location for introduction of a lead 104 or drug delivery catheter. Once the guide wire 102 is proximate the desired location, the delivery catheter 90 may be advanced over guide wire 102, with guide wire 102 disposed in delivery lumen 92. As the distal end 98 of catheter 90 is advanced over guide wire 102, the movable flap 100 deforms and moves to an up or open position, as shown in FIG. 5. Delivery catheter 90 may be advanced over guide wire 102 until side port 96 is proximate the desired location. In some embodiments, catheter 90 includes at least two electrodes for determining the desired location, as described above. Once the delivery catheter 90 (e.g., side port 96) is located in the desired position, the guide wire 102 may be withdrawn through distal end 104 of the catheter 90.

When guide wire 102 is withdrawn from delivery lumen 92, the movable flap 100 is no longer being deformed, and returns to a down or closed position, as shown in FIG. 6. In the closed configuration, the movable flap 100 forms a deflection surface which can deflect a lead 104 advanced through delivery lumen 92 out side port 96, as shown in FIG. 6.

A delivery catheter 90 including a single delivery lumen 92 and a movable flap 100 may provide a delivery catheter with a smaller outer diameter compared to a delivery catheter with both a delivery lumen and a guide wire lumen, such as catheter 60 of FIG. 4, while still permitting the use of a guide wire 102 during advancement of the catheter to a desired location within a patient. In embodiments where the lead 104 is to be delivered to a small diameter lumen, such as a small artery or vein, it may be desirable to form the delivery catheter 90 with as small an outer diameter as possible.

Figure 7:
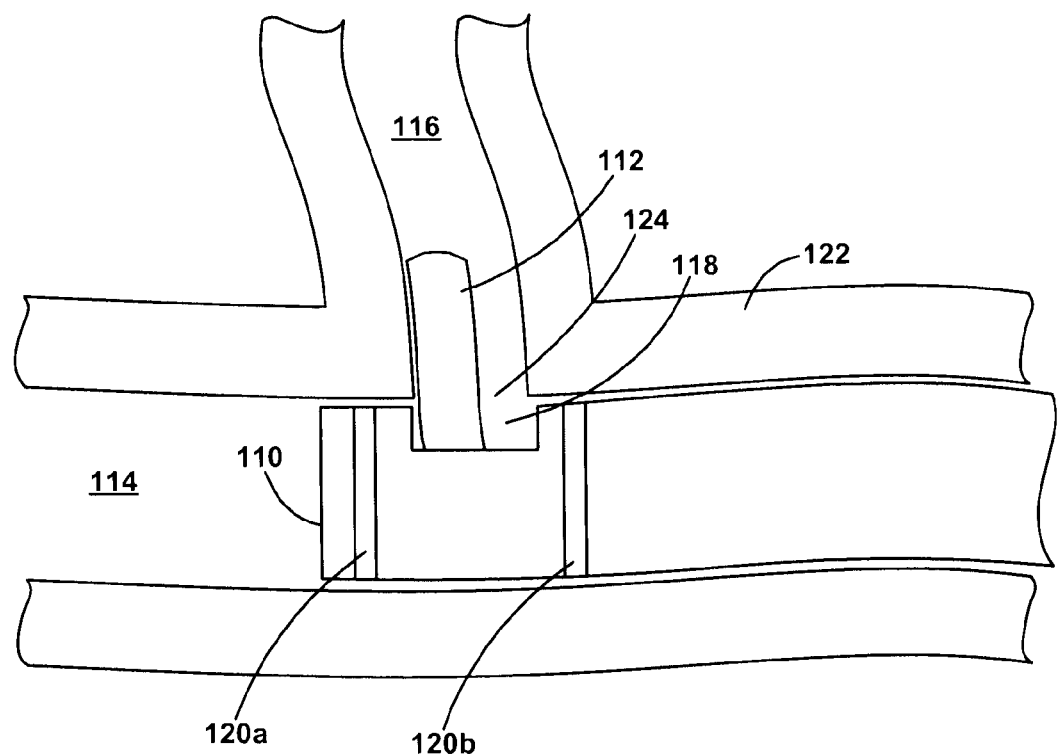
FIG. 7 is a schematic side view illustrating an example delivery catheter in a patient lumen and a lead exiting a side port and entering a second patient lumen.

While the disclosure hereinabove has been generally directed to delivery catheters for transvenous introduction of a stimulation lead to a location proximate the His bundle, delivery catheters according to this disclosure may find applicability in other situations. For example, as illustrated in FIG. 7, a delivery catheter 110 may be used to deliver a lead 112 to a location through the coronary sinus. In many cases, it is desired that the lead 112 be advanced through coronary sinus 114 and into a coronary vein 116. Some of the most desirable coronary veins 116 branch off coronary sinus 114 substantially perpendicularly. It may be difficult to direct the lead 112 or a conventional catheter from the coronary sinus 114 to the coronary vein 116 when the angle is substantially perpendicular. However, delivery catheter 110, which includes side port 118, facilitates the advancement of the lead 112 into coronary vein 116, as shown in FIG. 7.

Additionally, delivery catheter 110 includes a first electrode 120*a* distal from side port 118 and a second electrode 120*b* proximal from side port 118. In some embodiments, an ECG detected by electrodes 120*a* and 120*b* may be used to detect when catheter 110 is located within coronary sinus 114 proximate to coronary vein 116. For example, the presence of a relative large atrial depolarization wave, or P-wave, and a relatively small R-wave may indicate that catheter 110 is within coronary sinus 114 rather than RV 6. The physician may identify the opening into vein 116 and advance lead 112 into the vein by feel, utilizing fluoroscopy or other visualization techniques, or any other technique known in the art.

Additionally, the configuration of electrodes 120*a* and 120*b* may enable the detection of the location of coronary vein 116. For example, a voltage or current may be applied between first electrode 120*a* and second electrode 120*b* as the catheter is advanced through first coronary vein 114, and the impedance of vein wall 122 may be detected. When first electrode 120*a* is advanced adjacent the orifice 124 of second coronary vein 116, the detected impedance will change, indicating that an electrode is adjacent an orifice. In some embodiments, the delivery catheter 110 may be advanced further, until the impedance returns to a value indicating both electrodes are adjacent a vein wall 122. The lead 112 may them be advanced through a delivery lumen (not shown) in catheter 110, out side port 118, and into second coronary vein 116.

In another embodiment, a delivery catheter may be used to insert an epicardial lead through a minimally invasive substernal incision. For example, an incision may be made in the pericardium and the catheter may be advanced through the incision. In some embodiments, the catheter may be advanced over a guide wire and/or through a sheath that is positioned within and maintains an opening at the pericardial incision.

The delivery catheter may again include a first electrode, a second electrode, and a side port. The electrodes may be used to detect the ECG. The amplitude of the ECG may be used to distinguish epicardial and myocardial tissue unsuitable for pacing, e.g., ischemic or otherwise damaged or defective tissue, from epicardial and myocardial tissue which is suitable for pacing. In particular, the amplitude of the ECG will be discernibly lower when the electrodes are over or contacting unsuitable epicardial and myocardial tissue.

The electrodes may additionally or alternatively be used to detect impedance of the epicardial tissue with which the electrodes are in contact, which may additionally or alternatively be used to distinguish unsuitable, e.g., ischemic, epicardial and myocardial tissue unsuitable for pacing from living epicardial and myocardial tissue which is suitable for pacing. In particular, unsuitable tissue may have a higher impedance than viable tissue.

In either case, once a desired location for pacing is determined, a lead may be advanced through a delivery lumen defined in the catheter body and out of the side port. The lead may be attached to the epicardial tissue and the catheter withdrawn from the delivery site through the pericardial incision.

In some embodiments, the delivery catheter may include a pre-formed curvature similar to the natural curvature of the epicardium. Additionally, in some embodiments, the side port may be defined in a perimeter surface of the catheter which is disposed toward the epicardium when the catheter is allowed to relax towards its pre-formed curvature.

Further, delivery catheters described herein may find application delivering leads to other locations within a patient. For example, the delivery catheters described herein may be used to deliver leads for neurostimulation therapy (e.g., spinal cord stimulation), deep brain stimulation, stimulation of one or more muscles, muscle groups or organs, and, generally, stimulation of tissue of a patient. In other applications, the delivery catheters described herein can be used to deliver leads which provide muscular stimulation therapy, gastric system stimulation, nerve stimulation, lower colon stimulation, recording or monitoring, gene therapy, or the like.

Additionally, in some embodiments the delivery catheters described herein can be used to deliver catheters for dispensing a drug or other beneficial agent from an implanted or external drug delivery device. In short, the delivery catheters described herein can find useful application in delivery of a wide variety of leads or catheters for delivery of therapy to a patient or for patient sensing. The patient may be a human patient. In some cases, however, the delivery catheters described herein may be applied deliver leads or catheters to non-human patients.

Figure 8:
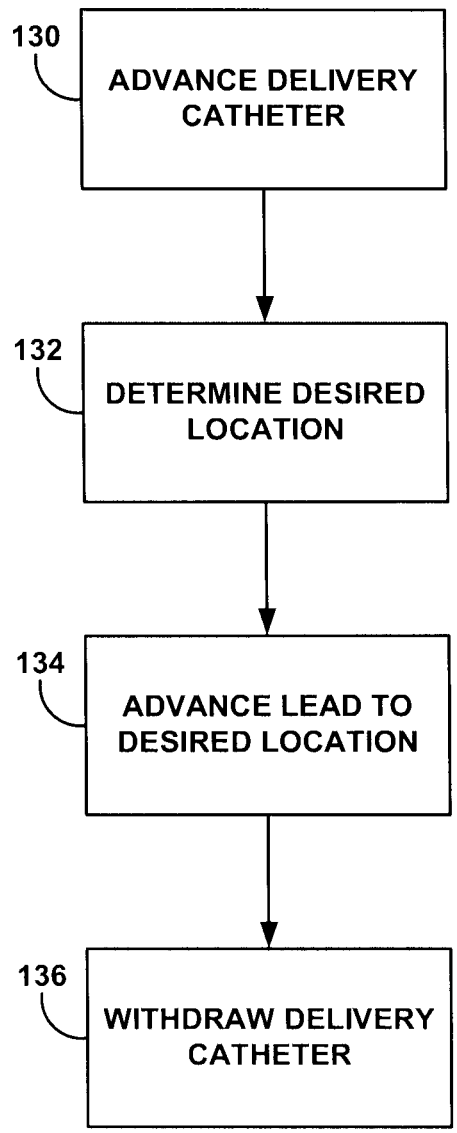
FIG. 8 is a flow diagram illustrating an example method of delivering a medical lead to a desired location using a delivery catheter.

FIG. 8 is a flow diagram that illustrates an example method of introducing a lead into a patient using a delivery catheter of the present disclosure, which, while any of the described catheters may be used, will be described with reference to the delivery catheter 8 and lead 25 of FIGS. 1 and 2.

First, the delivery catheter 8 is advanced proximate a desired location (130). In some embodiments, the delivery catheter 8 may be advanced transvenously through a SVC 12, into a right atrium 10, through a tricuspid valve 13 and into RV 6. In other embodiments, the delivery catheter 8 may be inserted into a torso through an incision and advanced through an incision in a pericardium to a location adjacent epicardial tissue. In yet other embodiments, the delivery catheter 8 may be advanced transvenously into a coronary vein. In some embodiments, the desired location may include a His bundle 3. In other embodiments, the desired location may include another coronary vein, an epicardial tissue which is not damaged or defective, or an endocardial tissue which is not damaged or defective.

Once the catheter 8 is proximate the desired location, electrodes 27 are used to determine the desired location (132). The desired location may be determined by detecting characteristics of a physiological waveform, e.g., a His spike within an ECG, or an impedance of tissue 29 adjacent electrodes 27.

After the desired location is determined, a lead 25 may be advanced within a delivery lumen (e.g., internal lumen 22), out of side port 9 and to the desired location (134). The lead 25 may then optionally be attached to the desired location, when the desired location comprises tissue 29, or the lead 25 may be advanced further, when the desired location comprises a second lumen.

Finally, the delivery catheter 8 is withdrawn from the patient (136). As described briefly above, in some embodiments the delivery catheter 8 may comprise a feature 24 oriented substantially longitudinally along perimeter surface 17 which enables delivery catheter 8 to be easily removed over lead 25 by, for example, tearing the catheter. In other embodiments, the catheter 8 may simply be withdrawn over a proximal end of lead 25.

Figure 9:
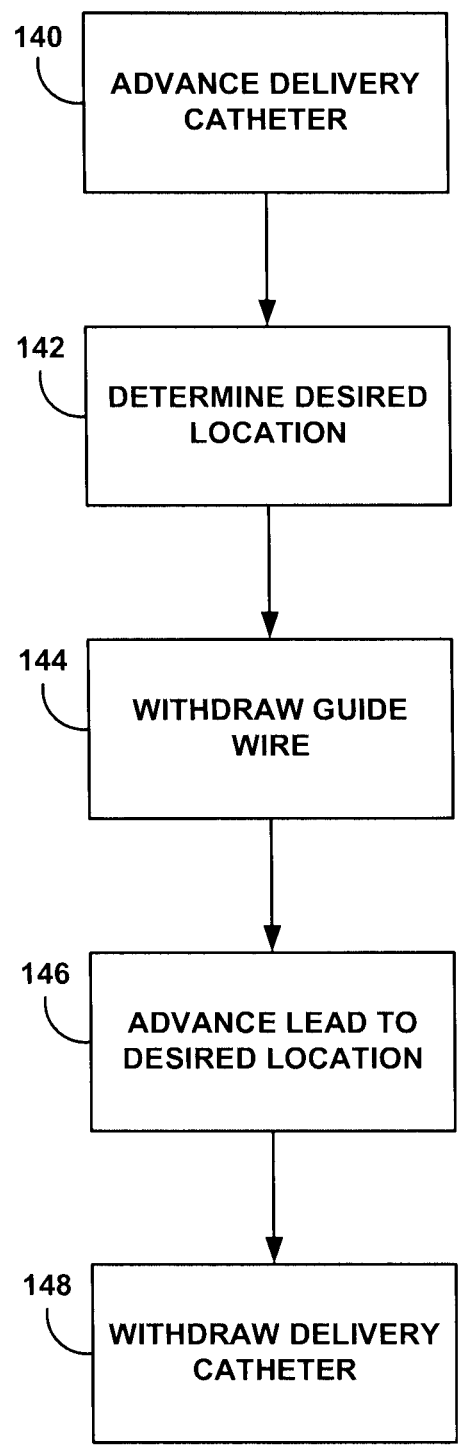
FIG. 9 is a flow diagram illustrating an example method of delivering a medical lead to a desired location using a delivery catheter and a guide wire.

FIG. 9 is a flow diagram that illustrates another example method of delivering a lead to a desired location in a patient using a delivery catheter. The method of FIG. 9 will be described with reference to delivery catheter 90 of FIGS. 5 and 6. Similar to the embodiment illustrated in FIG. 8, the delivery catheter 90, which includes a guide wire 102 disposed in delivery lumen 92, is advanced over the guide wire until it is proximate to a desired location (140). Guide wire 102 may have been previously advanced to the desired location, prior to advancing catheter 90 over the guide wire. Again, the desired location may be a His bundle, a coronary vein, an epicardial tissue which is not damaged or defective, or an endocardial tissue which is not damaged or defective.

The desired location is then determined using a first electrode and a second electrode (142). In the embodiment illustrated in FIG. 9, the guide wire 102 is then withdrawn (144) from delivery lumen 92. As the guide wire 102 is withdrawn, the movable flap 100 moves from an open position, shown in FIG. 5, to a closed position, shown in FIG. 6. This provides a deflection surface which can deflect a lead 104 out of side port 96.

A lead 104 is then advanced through delivery lumen 92 from a proximal end of delivery catheter 90. As the lead 104 is advanced and reaches movable flap 100, movable flap 100 deflects lead 104 out of side port 96 and to the desired location (146). The lead 104 may then optionally be attached to the desired location, when the desired location comprises tissue, or the lead 104 may be advanced further, when the desired location comprises a second lumen.

Finally, the delivery catheter 90 is withdrawn from the patient (148). As described briefly above, in some embodiments the delivery catheter 90 may comprise a feature (e.g., feature 24) oriented substantially longitudinally along a perimeter surface of catheter 90 which enables delivery catheter 90 to be easily removed over lead 104. In other embodiments, the catheter 90 may simply be withdrawn over a proximal end of lead 104.

Various embodiments have been described. However, one of ordinary skill in the art will appreciate that various modifications may be made to the described embodiments. For example, although described above with reference to embodiments in which a delivery catheter includes two electrodes proximate to the side port, the disclosure is not so limited. For example, delivery catheter embodiments according to the disclosure may include three or more electrodes, or may include a single electrode used with a remote and/or indifferent electrode for any of the detection purposes described herein.

Additionally, although described primarily with reference to embodiments in which a cardiac pacing/sensing or other electrical implantable medical lead is delivered using a delivery catheter, the disclosure is not so limited. Delivery catheters according to the present disclosure may be used to deliver other catheters used for delivery of drugs or agents, sensing, shunting, or any other medical purpose. Delivery catheters according to the present disclosure may additionally or alternatively be used to deliver microstimulators, sensors, or any other sensing and/or therapeutic device or element that is implantable within a patient. Such medical devices or elements may have any configuration known in the art. For example, implantable medical leads may have any number or type of electrodes coupled to one or more proximal connectors by one or more conductors within a flexible lead body. These and other embodiments are within the scope of the following claims.

The invention claimed is:

1. A system for implanting an implantable element proximate to the His bundle, wherein the implantable element is configured for at least one of therapy delivery or sensing proximate to the His bundle, and wherein the system comprises:

a delivery catheter comprising:
a catheter body comprising a proximal end, a distal end and a perimeter surface extending along a length of the catheter body between the proximal end and the distal end, wherein the catheter body comprises a longitudinal axis and defines a delivery lumen extending along the longitudinal axis within the catheter body;
a side port defined in the perimeter surface, orthogonal to the longitudinal axis, and proximate the distal end and in communication with the delivery lumen, wherein the implantable element is sized for delivery through the delivery lumen and out of the side port;
a first electrode; and
a second electrode, wherein each of the first and second electrodes is adjacent to and spaced from the side port; and
an external device,
wherein the delivery catheter comprises a connector at or near the proximal end to electrically couple the first and second electrodes to the external device,
wherein the first and second electrodes are configured to obtain an electrocardiogram of the patient,
wherein the external device is configured to receive the electrocardiogram from the first and second electrodes, analyze the electrocardiogram, and detect a signature waveform of the His bundle based on the analysis of the electrocardiogram, for implanting the implantable element at a location based on the detection of the signature waveform of the His bundle, and wherein the signature waveform comprises at least one of the atrial P-wave, ventricular QRS signature, and a His spike between the P-wave and QRS signature.

2. The system of claim 1, wherein the first and second electrodes are both distal from the side port.

3. The system of claim 1, wherein the first and second electrodes are both proximal from the side port.

4. The system of claim 1, wherein the first electrode is distal from the side port and the second electrode is proximal from the side port.

5. The system of claim 1, wherein each of the first and second electrodes are each spaced at least 2 mm from the side port.

6. The system of claim 1, wherein the catheter body further defines a guide wire lumen.

7. The system of claim 1,
wherein the catheter body further comprises a deflection member extending into the delivery lumen at a distal end of the side port, and
wherein the deflection member of the catheter body is configured to deflect the implantable element out of the side port.

8. The system of claim 7, wherein the deflection member terminates the delivery lumen.

9. The system of claim 7, wherein the deflection member comprises a flap moveable between an open position and a closed position.

10. The system of claim 9, wherein the flap is configured to be moved into the open position by a guide wire traversing the delivery lumen, move back into the closed position when the guide wire is removed from the delivery lumen, and deflect the implantable element that is delivered through the delivery lumen out of the side port when in the closed position.

11. The system of claim 1, wherein the distal end of the catheter body comprises a blind end.

12. The system of claim 1, wherein the delivery catheter is at least one of steerable or preformed with a curve proximate to the distal end.

13. A kit comprising:
a delivery catheter comprising:
a catheter body comprising a proximal end, a distal end and a perimeter surface extending along a length of the catheter body between the proximal end and the distal end, wherein the catheter body comprises a longitudinal axis and defines a delivery lumen extending along the longitudinal axis within the catheter body;
a side port defined in the perimeter surface, orthogonal to the longitudinal axis, and proximate the distal end and in communication with the delivery lumen;
a first electrode; and
a second electrode, wherein each of the first and second electrodes is adjacent to and spaced from the side port;
an implantable element for at least one of therapy delivery or sensing that is sized for delivery through the delivery lumen and out of the side port; and
an external device,
wherein the delivery catheter comprises a connector at or near the proximal end to electrically couple the first and second electrodes to the external device,
wherein the first and second electrodes are configured to obtain an electrocardiogram of the patient, wherein the external device is configured to receive the electrocardiogram from the first and second electrodes, analyze the electrocardiogram, and detect a signature waveform of the His bundle based on the analysis of the electrocardiogram, for implanting the implantable element at a location based on the detection of the signature waveform of the His bundle, and wherein the signature waveform comprises at least one of the atrial P-wave, ventricular QRS signature, and a His spike between the P-wave and QRS signature.

14. The kit of claim 13, wherein the implantable element comprises a medical lead.

15. The kit of claim 13, wherein the implantable element comprises another catheter.

16. The kit of claim 13,
wherein the catheter body of the delivery catheter further comprises a deflection member extending into the delivery lumen at a distal end of the side port, and
wherein the deflection member of the delivery catheter is configured to deflect the implantable element out of the side port.

17. The kit of claim 16, wherein the deflection member of the delivery catheter terminates the delivery lumen.

18. The kit of claim 16, wherein the deflection member of the delivery catheter comprises a flap moveable between an open position and a closed position.

19. The kit of claim 18, wherein the flap of the delivery catheter is configured to be moved into the open position by a guide wire traversing the delivery lumen, move back into the closed position when the guide wire is removed from the delivery lumen, and deflect the implantable element that is delivered through the delivery lumen out of the side port when in the closed position.

20. The kit of claim 13, wherein the distal end of the catheter body comprises a blind end.

21. A method comprising:
advancing a delivery catheter toward a desired location within a patient, wherein the delivery catheter comprises:
a catheter body comprising a proximal end, a distal end and a perimeter surface extending along a length of the catheter body between the proximal end and the distal end, wherein the catheter body comprises a longitudinal axis and defines a delivery lumen extending along the longitudinal axis within the catheter body,
a side port defined in the perimeter surface, orthogonal to the longitudinal axis, and proximate the distal end and in communication with the delivery lumen, wherein an implantable element is sized for delivery through the delivery lumen and out of the side port,
a first electrode, and
a second electrode, wherein each of the first and second electrodes is adjacent to and spaced from the side port;
identifying, via an external device, the desired location with the first electrode and the second electrode, wherein the delivery catheter comprises a connector at or near the proximal end to electrically couple the first and second electrodes to the external device, wherein the first and second electrodes are configured to obtain an electrocardiogram of the patient, wherein the external device is configured to receive the electrocardiogram from the first and second electrodes, analyze the electrocardiogram, and detect a signature waveform of the His bundle based on the analysis of the electrocardiogram, for implanting the implantable element at a location based on the detection of the signature waveform of the His bundle, and wherein the signature waveform comprises at least one of the atrial P-wave, ventricular QRS signature, and a His spike between the P-wave and QRS signature;

advancing the implantable element for at least one of therapy delivery or sensing through the delivery lumen and out the side port to the desired location; and withdrawing the delivery catheter from the patient.

22. The method of claim 21, further comprising attaching the implantable element to the desired location.

23. The method of claim 21, wherein the desired location comprises at least one of a living tissue, an epicardial tissue, an orifice, a patient lumen, or a coronary vein.

24. The method of claim 21, wherein the desired location comprises the His bundle.

25. The method of claim 24, wherein the implantable element comprises an implantable medical lead for at least one of stimulation or sensing.

26. The method of claim 21, wherein advancing a delivery catheter comprises advancing the delivery catheter over a guide wire disposed within the delivery lumen, and wherein the method further comprises removing the guide wire from the delivery lumen prior to advancing the implantable element through the delivery lumen and out the side port to the desired location.

27. The method of claim 26,
wherein the delivery catheter comprises a deflection member comprising a movable flap,
wherein the movable flap is in an open position when the guide wire is disposed within the delivery lumen,
wherein removing the guide wire from the delivery lumen moves the movable flap to a closed position, and
wherein advancing the implantable element comprises advancing the implantable element through the delivery lumen, and deflecting the implantable element off the moveable flap in the closed position and out the side port to the desired location.

28. The method of claim 21, wherein advancing the implantable element comprises advancing the implantable element through the delivery lumen, deflecting the implantable element off a deflection member and out the side port to the desired location.

29. The method of claim 21, wherein identifying the desired location comprises detecting an electrocardiogram via the first and second electrodes, and identifying the desired location based on the electrocardiogram.

30. The method of claim 29, wherein identifying the desired location comprises detecting a signature waveform of the His bundle via the first and second electrodes.

31. The method of claim 21, wherein the implantable element comprises an implantable medical lead.

\* \* \* \* \*

UNITED STATES PATENT AND TRADEMARK OFFICE
CERTIFICATE OF CORRECTION

PATENT NO. : 8,874,237 B2  
APPLICATION NO. : 12/103840  
DATED : October 28, 2014  
INVENTOR(S) : Richard John Schilling Page 1 of 1

It is certified that error appears in the above-identified patent and that said Letters Patent is hereby corrected as shown below:

In the Claims

On Column 13, Claim 10, Line 34: Replace "lumen, move back" with -- lumen, moved back --

On Column 14, Claim 19, Line 29: Replace "lumen, move back" with -- lumen, moved back --

Signed and Sealed this  
Eighteenth Day of July, 2017

Joseph Matal  
*Performing the Functions and Duties of the*  
*Under Secretary of Commerce for Intellectual Property and*  
*Director of the United States Patent and Trademark Office*